United States Patent [19]
Takasaki et al.

[11] 3,992,261
[45] Nov. 16, 1976

[54] METHOD FOR MANUFACTURE OF MALTOSE FROM STARCH BY ENZYMES CO-PRODUCED BY A SINGLE MICROORGANISM

[75] Inventors: Yoshiyuki Takasaki; Yoshimasa Takahara, both of Chiba, Japan

[73] Assignee: Agency of Industrial Science & Technology, Tokyo, Japan

[22] Filed: Jan. 6, 1975

[21] Appl. No.: 538,918

[30] Foreign Application Priority Data

Jan. 11, 1974 Japan.................................. 49-6465

[52] U.S. Cl................................. 195/31 R; 195/62; 195/66 R
[51] Int. Cl.².................. C12D 13/02; C12D 13/10; C07G 7/02
[58] Field of Search.................. 195/66 R, 65, 31 R, 195/62, 11, 7, 63, 68, 111, 114

[56] References Cited
UNITED STATES PATENTS

| | | | |
|---|---|---|---|
| 2,494,514 | 1/1950 | Liggett et al. | 195/114 |
| 3,677,896 | 7/1972 | Kurimoto et al. | 195/31 R |
| 3,769,168 | 10/1973 | Masuda et al. | 195/66 R |
| 3,804,718 | 4/1974 | Okada et al. | 195/66 R |
| 3,827,940 | 8/1974 | Sugimoto et al. | 195/66 R |

OTHER PUBLICATIONS

Zaborsky, *Immmobilized Enzymes*, CRC Press, Cleveland, Ohio, pp. 75–82 (1974).
Griffin et al., "Starch–Degrading System Elaborated by *Bacillus polymyxa*", *Chemical Abstracts*, vol. 79, Abs. No. 89195u, p. 182 (1973).
Griffin et al., "Production of an Amylolytic Enzyme by *Bacillus polymyxa* in Batch Cultures", *Chemical Abstracts*, vol. 79, Abs. No. 40920n, pp. 237–238 (1973).
Levine et al., *Compilation of Culture Media for the Cultivation of Microorganisms*.
Vainer et al., *Prikladnaya Biokhimiya i Mikrobiologiya* vol. 5, No. 3, pp. 364–366 (1969).

*Primary Examiner*—A. Louis Monacell
*Assistant Examiner*—Thomas G. Wiseman
*Attorney, Agent, or Firm*—Oblon, Fisher, Spivak, McClelland & Maier

[57] ABSTRACT

A microorganism which simultaneously produces β-amylase and dextrin α-1,6-glucosidase is cultured. By use of the enzymes thus produced, starch is directly hydrolyzed into maltose in a high yield.

9 Claims, 5 Drawing Figures

—○— β-Amylase
—●— α-1,6-glucosidase pH 4-6 acetate buffer
pH 6-10 phosphate buffer —○— β-Amylase
—●— α-1,6-glucosidase reaction time; 30 min.

—○— β-Amylase
—●— α-1,6-glucosidase

Temp. of treatment
: 30° C
Time of treatment
: 3 hours

METHOD FOR MANUFACTURE OF MALTOSE FROM STARCH BY ENZYMES CO-PRODUCED BY A SINGLE MICROORGANISM

BACKGROUND OF THE INVENTION

This invention relates to a method for the manufacture of maltose by use of enzymes which are produced by a single microorganism. More particularly, the present invention concerns a method for direct manufacture of maltose from starch by use of a microorganism capable of simultaneously producing $\beta$-amylase and $\alpha$-1,6-glucosidase.

Heretofore, $\beta$-amylase ($\alpha$-1,4-glucan maltohydrolase) has been found to occur mostly in malt and soybean. Commercially, these are used as sources for the enzyme today. Besides, microorganisms of genus *Bacillus* have been known to be capable of producing a similar enzyme. For example, Kneen et al. discovered in 1946 that *Bacillus polymyxa* produces $\beta$-amylase (Archives of Biochemistry, Vol. 10, p 41 (1946)) and, in 1948, Rose made a more detailed report on the enzymatic property of $\beta$-amylase produced by the strain of said microorganism (Archives of Biochemistry, Vol. 16, p 349 (1948)). After that, Higashihara et al. reported that *Bacillus megaterium* produces $\beta$-amylase (Japan Agricultural Chemical Society, Abstracts of Lectures at the 1971 Annual Meeting, p 212 and Amylase Symposium, Vol. 6, p 39 (1971)). It was reported that this enzyme is identical with the $\beta$-amylase produced by *Bacillus polymyxa* (Japan Agricultural Chemical Society, Abstracts of Lectures at the 1972 Annual Meeting p 86.

On the other hand, as concerns $\alpha$-1,6-glucosidase of starch, many reports so far made treat this enzyme as isoamylase or pullulanase. To be specific, isoamylase was first discovered to occur in yeasts by Maruo, Kobayashi et al. (Bunji Maruo and Tsuneo Kobayashi, Journal of Japan Agricultural Chemical Society, Vol. 23, pp 115 and 120 (1949). This enzyme has since been found to occur in higher plants (the enzyme from such source is referred to as R-enzyme) and in microorganisms of genus Pseudomonas (Japanese Patent Publication No. 16788/1970). More recently, a report was made to the effect that thermophilic *Bacillus stearothermophilas* produces a thermophilic isoamylase whose optimum working temperature is 65° to 67.5° C (Japan Agricultural Chemical Society, Abstracts of Lectures at the 1972 Annual Meeting, p 88 and Japanese Patent Disclosure No. 91272/1973).

Pullulanase was found by Bender in 1959 to occur in Aerobacter aerogenes as an enzyme capable of hydrolyzing the polysaccharide pullulan produced by *Pullularia pullulan*. It hydrolyzes the $\alpha$-1,6-glucosidasic linkage of pullulan to give rise to maltotriose (Biochem. Biophys. Acta, Vol. 36, p. 309 (1959) and Japanese Patent Publication No. 7559/1971). This enzyme also hydrolyzes the $\alpha$-1,6-glycosidasic linkage such as of amylopectin and glycogen. It has since been reported that enzymes of such description are also produced by microorganisms such as *Escherichia intermedia* (Ueda et al. Applied Microbiology, Vol. 15, p. 492 (1967)) and *Streptomyces mites* (Ueda et al., Journal of Fermentation Technology, Vol. 49, p 552 (1971)).

As described above, independent production of $\beta$-amylase and $\alpha$-1,6-glucosidase has been reported in numerous articles. However, no report has ever been made concerning a microorganism which produces both $\beta$-amylase and $\alpha$-1,6-glucosidase at the same time.

Therefore, it had been necessary to manufacture both enzymes by cultivating two different microorganisms separately. Besides, on account of the difference in the reaction pH and reaction temperature of the two enzymes, it has been difficult to react the enzymes upon starch at the same time. Therefore, the manufacture of maltose has heretofore been carried out by a two-step process which generally comprises first causing $\alpha$-1,6-glucosidase to react upon starch to produce a straight-chain amylose-like substance and subsequently having $\beta$-amylase react thereon to effect conversion to maltose.

SUMMARY OF THE INVENTION

An object of the present invention is to provide a method for producing, directly in high yields, maltose from starch by use of a microorganism capable of producing both $\beta$-amylase and $\alpha$-1,6-glucosidase at the same time.

To accomplish the object described above according to the present invention, there is provided a method for the manufacture of maltose which comprises causing bacteria of genus *Bacillus* capable of producing both $\beta$-amylase and $\alpha$-1,6-glucosidase at the same time to be cultured under conditions permitting production of said enzymes, collecting from the resultant culture the produced $\beta$-amylase and $\alpha$-1,6-glucosidase, adding the collected $\beta$-amylase and $\alpha$-1,6-glucosidase to starch or a starch derivative (solubilized starch, dextrin etc. and hereinafter referred to as "starch") and maintaining the resultant system under conditions permitting the starch to be hydrolyzed by said enzymes. When starch or a starch derivative is treated with the combined $\beta$-amylase and $\alpha$-1,6-glucosidase, the $\beta$-amylase functions to sever maltose units of amylopectin present in starch from the non-reducing ends of the chain and, as the severance has advanced to approach the branching linkage, the $\alpha$-1,6-glucosidase functions to sever the $\alpha$-1,6-glucosidase linkage of the branch and the $\beta$-amylase once again functions. Since the two enzymes, i.e. $\beta$-amylase and $\alpha$-1,6-glucosidase, alternately hydrolyze with maltose units of amylopectin from the non-reducing ends of the chain, maltose is produced directly by a one-step process from starch in yields higher than is attainable by the conventional method.

Figure 1:
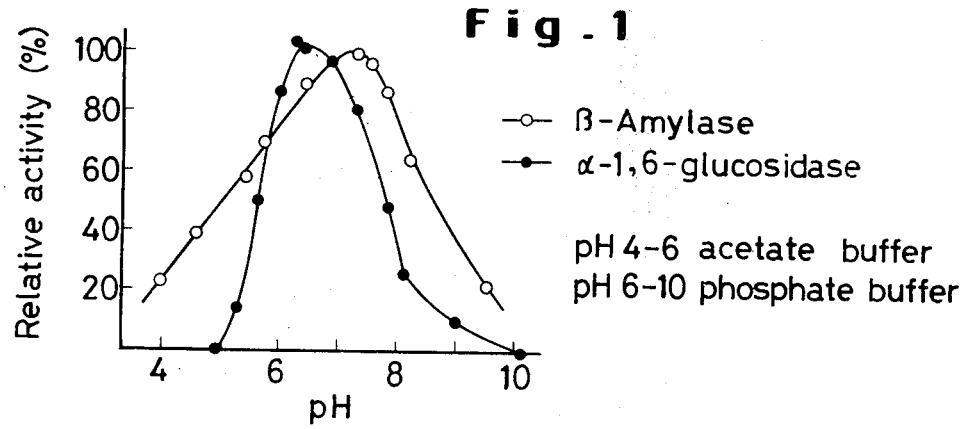
FIG. 1 is a graph showing the relation between the pH and the activity of $\beta$-amylase and $\alpha$-1,6-glucosidase produced by *Bacillus cereus* var. *mycoides*.

DETAILED DESCRIPTION OF THE INVENTION:

Entertaining a view that if $\beta$-amylase and $\alpha$-1,6-glucosidase both are produced at the same time, then they can be separated in the form of a compound enzyme preparation and can be employed as a highly advantageous enzyme for the production of maltose, the inventors have screened numerous microorganisms in search for species capable of producing both β-amylase and a type of α-1,6-glucosidase at the same time and consequently discovered three strains which are capable of producing both β-amylase and α-1,6-glucosidase at the same time.

All three of these strains are bacteria belonging to genus *Bacillus* and they have respectively been named *Bacillus cereus* var. *mycoides*, *Bacillus* sp. YT 1002 and *Bacillus* sp. YT 1003.

The present invention has been accomplished on the basis of this new knowledge. This invention permits maltose to be produced directly from starch and its derivatives by a method which comprises culturing bacteria belonging to genus *Bacillus* and having a capacity to produce both β-amylase and α-1,6-glucosidase at the same time, collecting from the resultant culture said two enzymes produced therein and treating the starch and its derivatives with the collected enzymes. No other microorganisms have so far been known to produce both β-amylase and α-1,6-glucosidase at the same time as is done by the bacteria of this invention.

These microorganisms have been deposited with the American Type Culture Collection under date of Dec. 26, 1974. The following ATCC numbers have been assigned to the microorganisms.

| | | |
|---|---|---|
| *Bacillus cereus* var. *mycoides*: | ATCC | 31102 |
| *Bacillus* sp. YT 1002: | ATCC | 31101 |
| *Bacillus* sp. YT 1003: | ATCC | 31103 |

The mycological characteristics of these microoganisms are as described hereinbelow.

*Bacillus cereus* var. *mycoides* (ATCC 31102)
 Rod, 1.1 to 1.4 by 4.2 to 7.0 μ, usually occuring in short to long chain like mold or Actinomyces. Non-motile. Gram positive. Sporangia, not appreciably swollen.
 Nutrient broth: Good growth, sediment.
 Nutrient agar slant: Growth abundant, Filamentous, Spreading, Creamy white.
 Glucose-asparagine agar: No good growth, Filamentous.
 Glucose-nitrate agar: No growth, or scant, if any.
 Tyrosine agar slant: Good growth, Filamentous, A little brown.
 Utilization of citrate: Positive.
 Milk: Peptonization.
 Potato: Good growth, Creamy white or a little brown.
 Gelatin: Liquefaction.
 Production of ammonia: Positive.
 Production of acetylmethylcarbinol: Positive.
 Reduction of nitrate to nitrite: Positive.
 Catalase: Positive.
 Production of indol: Negative.
 Hydrolysis of starch: Positive.
 NaCl broth: No growth in 4% NaCl broth.

*Bacillus* sp. YT 1002 (ATCC 31101)
 Rod 1–1.2 × 5–6 μ, Non-motile, Gram positive, Usually occuring in short to long chain.
 Nutrient broth: Sediment
 Nutrient agar slant: Good growth, Spreading
 Glucose-asparagine agar: Scant growth.
 Glucose-nitrate agar slant: Scant growth.
 Milk: Slow peptonization.
 Potato: Good growth, Spreading, Creamy white.
 Gelatin Liquefaction.
 Production of ammonia: Positive.
 Reduction of nitrate to nitrite: Positive.
 Catalase: Positive.
 Acetylmethylcarbinol: Produced.
 Citrate agar: Scant growth.
 Organic nitrogen source: Necessary for growth.
 Carbohydrate: Acid but no gas from glucose, fructose, galactose, mannose, lactose, maltose, trehalose, sorbit, glycerin, starch, glycogen.
 Temperature for growth: Grows until around 50° C. Optimum temperature 30°–35° C.
 Source: Isolated from soil.

*Bacillus* sp. YT 1003 (ATCC 31103)
 Rod, 1–1.6 × 2–7 μ, Usually occuring in short to long chain, Non-motile, Gram positive.
 Nutrient broth: Good growth, Sediment.
 Nutrient agar slant: Good growth, Spreading, Creamy White.
 Glucose-asparagine agar: Growth scant.
 Milk: Peptonization without coagulation.
 Gelatin: Slow liquefaction.
 Production of ammonia: Positive.
 Reduction of nitrate to nitrite: Positive.
 Catalase: Positive.
 Acetylmethylcarbinol: Produced.
 Citrate: Utilized as a carbon source.
 Carbohydrate: Utilized without gas formation, glucose, fructose, galactose, mannose, L-arabinose, D-xylose, sucrose, lactose, maltose, trehalose, raffinose, mannit, sorbit glycerin, inulin.
 Temperature of growth: Optimum temperature of growth, 30°–35° c, Maximum temperature 45° C.
 Source: Isolated from soil.

The species of bacteria according to the present invention invariably produce both β-amylase and α-1,6-glucosidase when they are cultured in a medium incorporating carbon sources and nitrogen sources of the type generally adopted for microorganic culture. Examples of carbon sources include maltose, starch, partial hydrolyzates of starch such as a dextrin and other forms of starch. Examples of nitrogen sources are peptone, casein, meat extract, yeast extract, corn steep liquor, soybean and soy cake. Where necessary to supplement said nitrogen sources, inorganic salts sources such as phosphate, magnesium salts, barium salts and calcium salt, and inorganic nitrogen source may be incorporated in the medium. Where corn steep liquor is used as a raw material for the medium, it is best adjusted in advance to pH 6 to 9 so that the resultant precipitate, namely a substance containing matter inhibiting the production of β-amylase, will be removed prior to use. Table 1 clearly indicates that when this precipitated matter is removed, the amount of β-amylase produced is more than 10 times greater than when the matter is not removed and that the removal of the precipitated matter only very slightly effects the production of α-1,6-glucosidase.

Table 1

| pH of treatment of corn steep liquor | β-amylase (units/ml broth) | α-1,6-glucosidase (units/ml broth) |
|---|---|---|
| Unadjusted | 40 | 35.4 |
| pH 5.1 ± 0.1 | 121 | 40.6 |
| pH 6.0 ± 0.1 | 420 | 39.1 |
| pH 7.1 ± 0.1 | 516 | 41.3 |

Table 1-continued

| pH of treatment of corn steep liquor | β-amylase (units/ml broth) | α-1,6-glucosidase (units/ml broth) |
| --- | --- | --- |
| pH 8.1 ± 0.1 | 525 | 35.9 |
| pH 9.1 ± 0.1 | 460 | 35.1 |
| pH 10.0 ± 0.1 | 352 | 25.0 |

With a view to producing the two enzymes in higher yields, the inventors made an elaborate study on conditions of culture. They have consequently ascertained that by incorporation of manganese ions in the medium, the production of α-1,6-glucosidase can be notably increased. The presence of manganese ions, however, has a rather inhibitory effect on the production of β-amylase. By appropriately selecting the time for and the added amount of manganese ions to the medium, therefore, the culture can be carried out so as to produce β-amylase and α-1,6-glucosidase both to desired concentrations.

As manganese salts, there can be used various manganese compounds. Examples thereof are manganese sulfate, manganese chloride, manganese phosphate, and manganese acetate. These manganese salts are generally added to the medium in an amount of from $1 \times 10^{-8}$ to $1 \times 10^{-2}$ mole, preferably from $1 \times 10^{-6}$ to $1 \times 10^{-4}$ mole. When the culture is carried out in a medium incorporating therein manganese sulfate in an amount of $1 \times 10^{-5}$ mole, for example, the amount of α-1,6-glucosidase is found to be 3 to 6 times as large as when said incorporation is omitted. In the production of the two enzymes, when the culture is carried out in a medium incorporating citrate and/or tartarate, both β-amylase and α-1,6-glucosidase are found to be produced in increased amounts. The citrate or tartarate is generally added to the medium in an amount of 0.01 to 1%, preferably 0.05 to 0.2%, based on the medium. When the culture is carried out in a medium incorporating sodium citrate or sodium tartarate in an amount of 0.1% based on the medium, for example, the amount of β-amylase produced is 1.5 to 2 times as large and that of α-1,6-glucosidase produced is about 1.3 to 1.5 times as large as when said incorporation of the salt is omitted.

Further, the inventors have found that when the culture is carried out in a medium incorporating rape-seed, rape-seed cake or an extract (a substance extracted from rape-seed by heating in water or a liquid having alkalinity of pH 9 to 10), the amount of α-1,6-glucosidase produced is increased to a notable extent. When the medium contains 4% of rape-seed cake, for example, the amount of α-1,6-glucosidase produced is 2 to 3 times as large as when said addition is omitted.

The culture of bacteria is carried out under aeration at 20° to 40° C for 24 to 72 hours. During the culture, the pH value of the medium varies in the range of from 5.5 to 9.5. It is desirable that the pH value of the medium be maintained in the range of from 6 to 8 throughout the entire course of culture.

Both β-amylase and α-1,6-glucosidase are produced extracellularly. The enzymes thus produced in the culture can be recovered by filtering the culture broth to remove the microorganic cells, concentrating the filtrate, and thereafter further effecting additional concentration by adding to the concentrated filtrate an organic solvent such as acetone, ethanol, methanol or isopropanol to cause precipitation or by adding a salt such as ammonium sulfate to promote the precipitation, for example. When the enzyme precipitation is promoted by the addition of ammonium sulfate a precipitate of 60 to 100% of β-amylase and α-1,6-glucosidase in a mixed state can be obtained at about 70 to 75% of saturation of ammonium sulfate.

Since either or both of the two enzymes are effectively adsorbed by starch, activated carbon, various kinds of diatomaceous earth such as Celite, Hyfro-Supercel or Perlite, various kinds of clay such as bentonite, acid clay, Fullernarde, Kaolin or talcum or calcium phosphate, they can be recovered by use of such an adsorbent. For example, β-amylase is effectively adsorbed on starch, particularly on starch which has undergone thermal treatment at 40° to 65° C. When corn starch is added to the culture broth, it adsorbs 3000 to 8000 units of β-amylase per g when it is pretreated at temperatures in the range of from 40° to 65° C as shown in Table 2. Also gelatinized starch provides effective adsorption of the enzyme.

Table 2

| Temperature of treatment of starch (° C) | Time (min.) | Activity of β-amylase absorbed (units/g of starch) |
| --- | --- | --- |
| 40 | 10 | 3,010 |
| 50 | 10 | 5,930 |
| 55 | 10 | 6,890 |
| 60 | 10 | 7,650 |
| 65 | 10 | 8,130 |
| 80 | 10 (Gelatinized) | 7,890 |
| Non-treatment | | 1,020 |

The adsorbed β-amylase can be completely eluted with a solution containing 1 to 10%, preferably 5 to 10%, of maltose or a solution containing soluble starch, dextrin or maltose. And, β-amylase and α-1,6-glucosidase are both adsorbed satisfactorily on activated carbon. The resultant adsorbed enzymes possess strong enzymatic activity and, therefore, can be used as immobilized enzymes. For example, β-amylase is adsorbed at a ratio of 8000 to 12000 units and α-1,6-glucosidase at a ratio of 500 to 1000 units respectively per g of active carbon. Of the resultant adsorbed enzymes, β-amylase retains an enzymatic activity equivalent to 90% of its original activity and α-1,6-glucosidase retains the same enzymatic activity (100%) as the original activity.

In addition dextrin, α-1,6-glucosidase is sufficiently adsorbed (500 to 800 units per g) on a diatomaceous substance such as Celite, Perlite etc. which is a siliceous substance or by a clay such as bentonite, acid clay or Kaolinite which is composed preponderantly of silica-alumina and the adsorbed enzyme can be completely eluted by an aqueous 5 to 10% sodium chloride solution. Even in this adsorbed state, the enzyme has an enzymatic activity correspondong to about 50 to 70% of the original activity.

Figure 3:
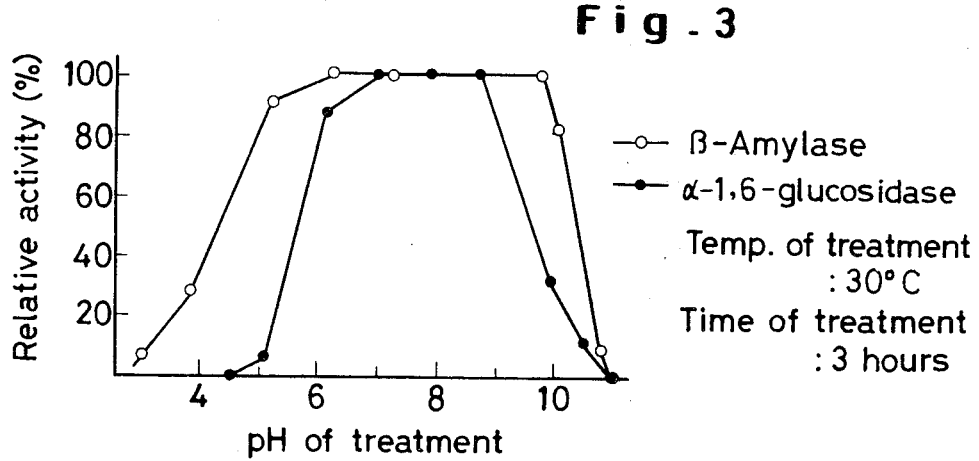
FIG. 3 is a graph indicating the pH stabilities of the two enzymes.
Figure 4:
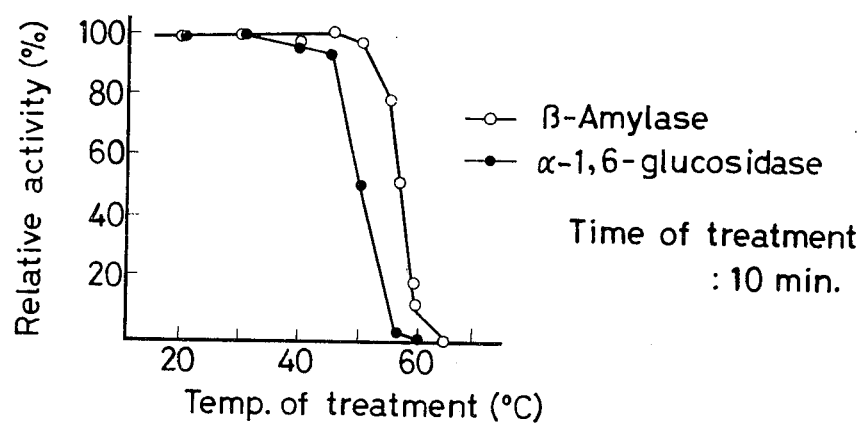
FIG. 4 is a graph showing the heat stability of the two enzymes.

The enzymatic character of β-amylase and α-1,6-glucosidase produced by the bacteria of the present invention are as shown below.

β-Amylase:
1. Action: The enzyme produces maltose from starch, amylose, amylopectin, glycogen, dextrin, etc.
2. Substrate specificity: The degree of hydrolysis as maltose for amylose is nearly 100% and nearly 60% for starch. Then enzyme does not hydrolyze α-1,6- glucosidasic linkage which is contained in amylopectin, glycogen, dextrin, pullulan, etc.
3. pH of action: pH 3 to 10 (FIG. 1)
4. Optimum pH: Around pH 7 (FIG. 1)
5. Temperature of action: Up to about 65° C (FIG. 2)
6. Optimum temperature: About 50° C (FIG. 2)
7. Inactivation: About 20% of activity is lost after 10 minutes' standing at 55° C. Substantially total loss of activity results after 10 minutes' standing at 70° C. (FIG. 4)
8. pH stability: This enzyme is unstable on the acid side below pH 5 and is stable on the alkali side in the range of pH 6 to 10. (FIG. 3)
9. Inhibition: This enzyme is inhibited by p-chloromercury benzoate and is little inhibited by monoiodoacetate. The activity inhibited by p-chloromercury benzoate is recovered by addition of cysteine. This enzyme is strongly inhibited also by $Cu^{++}$, $Hg^{++}$ and $Ag^+$. It is also inhibited by $Fe^{++}$.
10. Method of purification: The enzyme is fractionated by means of precipitation by 30–50% saturation of ammonium sulfate from the culture broth, and then highly purified by column chromatography using Sephadex G-100.
11. Measurement of the enzyme activity: A suitable amount of the enzyme solution is added to 2 ml of 0.1M phosphate buffer solution (pH 7.0) containing 2% of soluble starch and the resultant mixture is made up to a total volume of 4 ml with distilled water. The mixture is incubated at 40° C. The amount of enzyme which produces 1 mg of maltose after one hour of the reaction under the conditions described is defined as "1 unit".

α-1,6-Glucosidase:
1. Action: This enzyme hydrolyzes the α-1,6-glucosidasic linkage of the amylopectin which has been hydrolyzed to some extent by the action of β-amylase.
2. Substrate specificity: This enzyme produces maltotriose by hydrolizing the α-1,6-glucosidasic linkage of pullulan. When it is allowed to react upon amylopectin, no increase of iodine staining power is recognized. It is, therefore, inferred that this enzyme manifests its activity on amylopectin which has been hydrolyzed by β-amylase to some extent so that the side chain is cut short. However, the enzyme does not act on isomaltose and pannose.
3. pH of action: pH 5 to 10 (FIG. 1)
4. Optimum pH: pH 6 to 6.5 (FIG. 1)
5. Temperature of action: Up to about 65° C (FIG. 2)
6. Optimum temperature: About 50° C (FIG. 2)
7. Inactivation: About 50% of activity is lost after 10 minutes' standing at 50° C. Substantially total loss of activity results after 10 minutes' standing at 65° C. (FIG. 4) However, $Ca^{++}$ or $Sr^{++}$ shows a strong protective activity. In the absence of $Ca^{++}$, about 90% of activity is lost after 30 minutes' standing at 50° C. In the presence of $5 \times 10^{-3}$ M of $CaCl_2$, loss of activity is hardly recognized.
8. pH stability: The pH stability of this enzyme is in the range of from pH 6 to 9. The enzyme is unstable on the acid side of relatively stable on the alkali side (FIG. 3)
9. Inhibition: This enzyme is slightly inhibited by p-chloromercurybenzoate and is inhibited very little by monoiodoacetate. It is, however, inhibited seriously by $Hg^{++}$ and $Ag^{++}$. It is likewise inhibited by $Fe^{++}$.
10. Method of purification: This enzyme is fractionated by means of precipitation by 60–70% saturation of ammonium sulfate from the culture broth and then highly purified by Sephadex G-100 column chromatography.
11. Measurement of enzymatic activity: The activity of this enzyme is measured by the reaction using pullulan as the substrate under the following conditions. The enzyme produces maltotriose from pullulan.

A suitable amount of the enzyme is added to 0.5 ml of 0.1M phosphate buffer solution (pH 7.0) containing 1% of pullulan. The resultant mixture is made up to a total volume of 1.0 ml with distilled water. This mixture is incubated at 40° C for 1 hour.

The amount of the enzyme which produces 1 mg of maltotriose under the conditions described above is defined as "1 Unit".

From the physical and chemical properties, particularly the substrate specificity, described above, this enzyme is recognized to be a new α-1,6-glucosidase produced by genus Bacillus which cannot be classified under either of the heretofore known enzymes, isomaylase and pullulanase. It may as well be designated as dextrin α-1,6-glucosidase.

The α-1,6-glucosidases (isoamylase and pullulanase) produced by the microorganisms known to the art prior to the present invention invariably hydrolyze the α-1,6-glucosidasic linkage in the side chain of amylopectin to produce any amylose-like substance which shows a blue color in the iodine test (Biochemische Zeitshrift, Vol. 334, pp 79–95 (1961), Biochem, J., Vol. 108, pp 33–40 (1968), Biochimica et Biophsica Acta, Vol. 212, pp 458–469 (1970), J. Fermentation of Technology, Vol. 49, pp 552–559 (1971), etc.) Generally, therefore, the assay of these enzymes is carried out by measuring the increase of iodine staining power when the enzymes are allowed to react upon starch or amylopectin.

The α-1,6-glucosidase which is produced by the bacteria of the present invention is scarcely recognized to bring about any increase of iodine staining power when the enzyme is allowed to react upon starch or amylopectin. This fact indicates that the present enzyme reacts only on starch or amylopectin in which the side chain has been hydrolyzed to some extent by the action such as of β-amylase and the glucose residue in the side chain has consequently been cut short. This substrate specificity constitutes one leading feature which distinguishes the enzyme from the α-1,6-glucosidase produced by the conventionally known microorganisms.

Thus, the α-1,6-glucosidase which is produced by the strains belonging to genus *Bacillus* of the present invention is possessed of highly advantageous enzymatic properties whereby the enzyme cooperates with the simultaneously produced β-amylase to hydrolyze starch directly into maltose. As shown in FIG. 1 through FIG. 4, the two enzymes are quite similar to each other not merely in pH of action and optimum pH of action but equally in temperature of action and optimum temperature of action. They also bear a notable similarity in range of pH stability and condition of temperature stability. Concerning the mode of hydrolysis of the two enzymes, β-amylase severs the amylopectin in starch in the maltose units from the non-reducing ends of the chain and, when the rupture of the chain has approached the branching linkage, the α-

1,6glucosidase of the present invention functions to sever the α-1,6-glucosidasic linkage of the branch. Thus the two enzymes, β-amylase and α-1,6-glucosidase, alternately hydrolyze amylopectin into maltose units sequentially from the non-reducing ends. As may easily be expected from the mechanism of reaction, use of the enzyme of the present invention in conjunction with β-amylase provides maltose in yields higher than by use of any other heretofore known α-1,6-glucosidase, said yields approximating the theoretical yield (90–96%).

Where there is used a heretofore known enzyme such as pullulanase or isoamylase, the enzyme reacts upon the starch by severing the amylopectin branch in the starch to produce a straight-chain amylose-like substance and, subsequently, β-amylase is allowed to react on the amylose like substance so as to effect formation of maltose. It has been reported that by this continuous two-step process, maltose can be produced in favorable yields. When the enzymes of the present invention are used, however, it is difficult with such two-step process to produce maltose in the high yields attainable by the method of this invention. As described previously, in the present invention, the β-amylase and α-1,6-glucosidase alternately react to produce maltose and, therefore, the maltose can be produced in notably high yields.

Unlike isoamylases of yeast and *Pseudomonas* genus origin, the enzymes of the present invention hydrolyze the α-1,6-glucosidasic linkage of pullulan and eventually hydrolyzes pullulan completely into maltotriose. Of course, they can be used for producing maltotriose from pullulan. In the final product, the formation of glucose, maltose or oligosaccharide is not observed. The mode of hydrolysis involved in this case is judged to be of the oxo-type from the observation that formation of maltotroise occurs from the initial stage of reaction. The reaction caused by the present enzymes was not found to be reversible.

In contrast, in the hydrolysis of pullulan by the pullulanase produced by microorganisms of genus *Aerobacter* and genus *Streptococcus*, the formation of glucose, maltose, maltotetraose and still larger oligosaccharides as well as maltotroise has been observed (Biochemische Zeitschrift, Vol. 334 pp 79–95 (1961)) and the reverse reaction resulting in the formation of G6 compound from maltotriose and of G4 compound from maltose has been observed (Nature, Vol. 210, p 200 (1966), Archives of Biochemistry and Biophysics, Vol. 137, pp 483–493 (1970), Biochemical J., Vol. 108, pp 33–40 (1968), etc.), indicating that complete hydrolysis of pullulan to maltotriose is not attained.

As described previously, the present enzymes have high affinity for the hydrolysis of the short side chain of glucose residues and are incapable of hydrolyzing the α-1,6-glucosidasic linkage in isomaltose, pannose and isomaltotriose. These observations prove the enzymes to differ from the animal oligo-1,6-glucosidase (J. Biol. Chem., Vol. 215, pp 723–736 (1955)).

The α-1,6-glucosidase of the present invention is notably different from the heretofore reported isoamylase and pullulanase in terms of substrate specificity which is one of the most important properties of any enzyme. It is a fact that the α-1,6-glucosidase of this invention does not exhibit reversibility of reaction. Thus, this enzyme is different from the known pullulanase and isoamylase enzymes. Besides, the present α-1,6-glucosidase enzyme is protected from thermal inactivation by the addition of $Ca^{++}$ which does not occur with the known pullulanase and isoamylase enzymes. On the other hand, the phenomenon of recovery from thermal inactivation which is observed with the pullulanase from genus *Aerobacter* and genus *Streptococcus* is not recognized to occur in the case of the present enzyme. These phenomena indicate that the present enzyme is different from the pullulanase, etc. from genus *Aerobacter* and genus *Streptococcus* in terms of proteinaceous characteristics.

Figure 2:
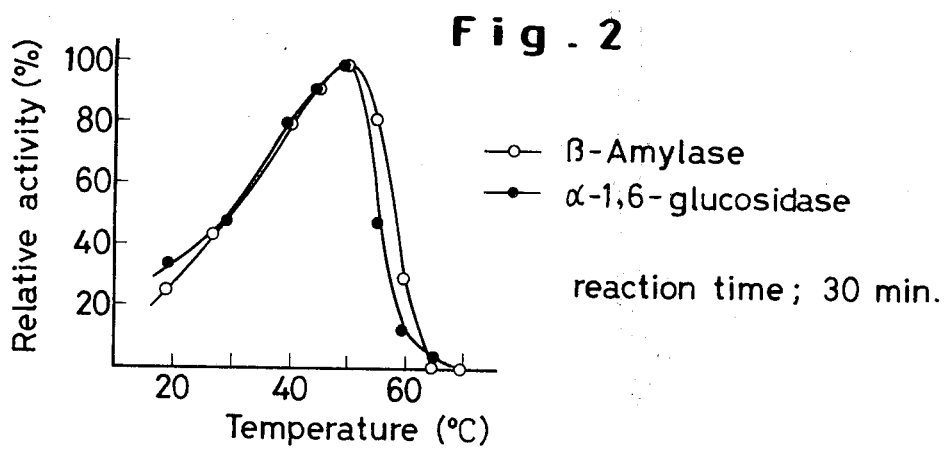
FIG. 2 is a graph indicating the relation between the temperature and the activity of said two enzymes.

The present enzyme exhibits an optimum pH of action in the neighborhood of neutrality as shown in FIG. 1 and an optimum temperature of action around 50° C as shown in FIG. 2. The pH and temperature characteristics of the present enzyme differs from pullulanase produced by genus *Aerobacter* (optimum pH of action 5.0, optimum temperature of action 47.5° C; Biochemische Zeitschrift, Vol. 334, pp 79–95 (1961)) and from pullulanase produced by genus *Streptococcus* (optimum pH of action 5.4–5.8, optimum temperature of action 30° C; Biochemical J., Vol. 108, pp 33–40 (1968) and also differs from the isoamylase of yeast (optimum pH of action 6.0–6.2, optimum temperature of action 20° C; Journal of Agricultural Chemical Society, Vol. 23, pp 115 and 120 (1949)) and the isoamylase produced by genus *Pseudomonas* (optimum pH of action 3–4, optimum temperature of action 52° C, Biochimica et Biophysica Acta, Vol. 212, pp 458–469 (1970)).

The filtrate of the culture broth resulting from the culture of the bacteria of the present invention, the concentrate of the filtrate, the precipitate recovered with organic solvent and the precipitate recovered with ammonium sulfate, all contain β-amylase and α-1,6-glucosidase and, therefore, can be used as a compound enzyme preparation for the production of maltose from starch, etc.

From this compound enzyme preparation, β-amylase and α1,6-glucosidase can be independently fractionated by saturating the liquid to 30–50% with ammonium sulfate to cause precipitation of the former enzyme and then saturating the liquid to 60–70% with the same compound to cause precipitation of the latter enzyme. The fractionated β-amylase and α-1,6-glucosidase can be refined to a high extent by Sephadex column chromatography.

Now, a description will be made of a method for producing maltose from starch by the use of the complex enzyme which is produced by the bacteria of the present invention.

When the bacteria of the present invention are cultured in the aforementioned manner, both β-amylase and α-1,6-glucosidase are produced in the culture broth. The culture broth is filtered or centrifuged to remove the microorganic cells, then added to starch solution. For higher yields of maltose, it is desired to use starch or soluble starch in low D.E. (Dextrose Equivalent:

$$\frac{\text{reducing sugar expressed as glucose}}{\text{dry substance}} \times 100 \text{ )}$$

Where a highly concentrated starch is offered to be hydrolyzed, the starch is liquefied by the action of α-amylase and the resultant liquefied starch is put to use. Dextrin and other similar substances are also usable as the substrate. The concentration of the substrate is in the range of from 5 to 60%, more ordinarily from 10 to 40%. Where necessary, calcium ions are added. The mixture is maintained at pH 5–8, preferably 6–7, and at a temperature in the range of from 20° to 60° C, preferably from 40° to 55° C, and then the culture broth containing the two enzymes, α-amylase and α-1,6-glucosidase, is added to the mixture. The precipitate containing the two enzymes or activate carbon having the two enzymes adsorbed thereon can be added to the reaction solution in place of the culture broth containing the two enzymes. It is also permissible for the two enzymes to be separated from the culture broth independently by virtue of adsorption or extraction and to be added to the reaction solution at the same time. The amount of β-amylase to be added generally ranges from 200 to 400 units and that of α-1,6-glucosidase ranges from 10 to 50 units per g of starch on a dry basis. Under these conditions, the starch is hydrolyzed into maltose in a yield of 80–90% after 48 to 72 hours of reaction. Of course, the reaction time is shortened when the amount of the enzymes added thereto is greater than the aforementioned range or the concentration of the substrate is lower.

As is clear from the foregoing detailed description, the two enzymes, β-amylase and α-1,6-glucosidase, are formed at the same time by cultivating a single strain and the compound enzyme preparation, when allowed to react upon starch or its derivatives, produces maltose directly. Thus, the method of the present invention enjoys not merely simplicity of operation but also enhancement of yields as compared with the conventional reaction process or with the method whereby two enzymes produced separately by two different strains are added to the reaction solution together.

Further, the ratio at which the two enzymes are to be produced by the culture can easily be adjusted as desired by controlled incorporation of manganese ions. It is also possible to increase the activity of both enzymes as desired by use of varying kinds of additives. Moreover, the two enzymes produced in the culture broth can easily be recovered and refined simultaneously or separately of each other. Thus, the present invention finds extensive utility in various industrial applications.

Preferred embodiments of the present invention will be described herein below. It should be understood that the present invention is not limited to these examples.

EXAMPLE 1

In an Erlenmeyer flask of 200 ml-capacity was placed 50 ml of a medium containing 1% of peptone, 0.3% of $K_2HPO_4$, 0.1% of $MgSO_4 \cdot 7H_2O$ and 1% of maltose. The medium was sterilized by an ordinary method (121° C, 15 minutes) and *Bacillus cereus* var. *mycoides* (FERM No. 2391) was inoculated to the medium and cultured at 30° C for 2 days. After the culture, the culture broth was centrifuged to remove the cells. Then the supernatant obtained was assayed to determine the amount of produced enzymes. There were formed 628 units of β-amylase and 18 units of dextrin α-1,6-glucosidase respectively per ml of the medium.

The culture broth was placed in a cellophane tube and dialyzed against distilled water to remove the residual sugar.

Part of said dialyzed enzymes (having 204 units of β-amylase and 3.6 units of dextrin α-1,6-glucosidase) was caused to react upon potato amylose, amylopectin, potato starch, glycogen and dextrin, each of 0.4% concentration, at pH 7, 40° C of temperature (total reaction volume 4.3 ml).

Figure 5:
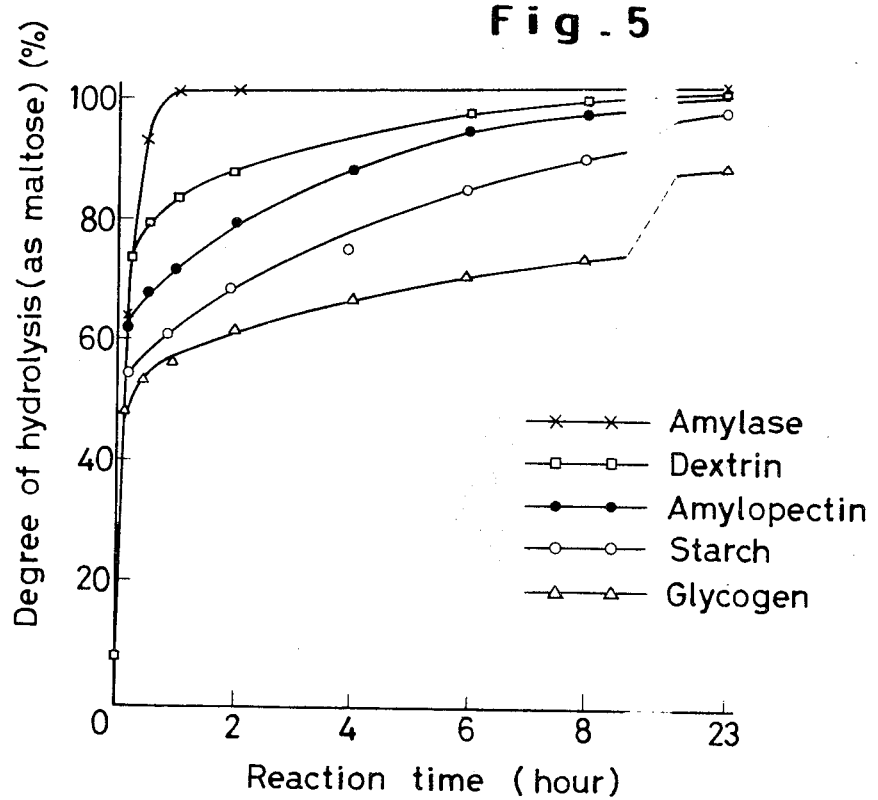
FIG. 5 is a graph showing the relation between the reaction time and the degree of hydrolysis (as maltose) determined when the cultured broth of said microorganism was caused to react upon amylose, amylopectin, potato starch, glycogen and dextrin.

At fixed intervals along the course of time, the reaction solution was sampled each in a fixed amount and, reducing sugar formed was determined by the Somogyi & Nelson method. Sugar composition of the reaction mixture was tested by paper chromatography (4 parts of pyridine, 6 parts of butanol and 3 parts of water). Consequently, it was confirmed that the formed sugar was almost completely maltose (90–96%) when amylose, amylopectin or potato starch was used as the substrate and a very small amount of sugar having the Rf corresponding to maltotriose was observed in the final reaction solution (4–8%). A test by Glucostat (made by Worthington Biochemical Corporation, U.S.A.) revealed that the formation of glucose was in an extremely small percentage (less than 0.1%). The results obtained are shown in FIG. 5. It is seen from FIG. 5 that potato amylose, amylopectin, dextrin and potato starch thus tested were all hydrolyzed substantially completely into maltose after about 8 hours of reaction. Glycogen was also hydrolyzed at a perentage of not less than 90% into maltose after about 23 hours of reaction.

EXAMPLE 2

In a medium having the same composition as used in Example 1, *Bacillus* sp. YT-No. 1002 (FERM No. 2837) was inoculated and subjected to shaken culture at 30° C. After 48 hours of culture, the culture broth was assayed for the amount of enzymes formed. There were formed 121 units of dextrin β-amylase and 10.5 units of α-1,6-glucosidase respectively per ml of broth.

EXAMPLE 3

In a medium having the same composition as used in Example 1, *Bacillus* sp. YT-No. 1003 (FERM No. 2838) was inoculated and subjected to shaken culture at 30° C. After 48 hours of culture, the culture broth was assayed for the amount of enzymes formed. There were formed 152 units of β-amylase and 5.3 units of dextrin α-1,6-glucosidase respectively per ml of broth.

EXAMPLE 4

In a flask having 1 liter-capacity, 250 ml of a medium containing 1% of polypeptone, 0.3% of $K_2HPO_4$, 0.1% of $MgSO_4 \cdot 7H_2O$ and 1% of dextrin was placed and sterilized by the conventional method. Thereafter *Bacillus cereus* var. *mycoides* was inoculated to the medium and subjected to shaken culture at 30° C. After 48 hours of culture, the culture broth was centrifuged to remove the cells and supernatant obtained was tested for enzymatic activity.

The test revealed that there were formed 420 units of β-amylase and 7.8 units of dextrin α-1,6-glucosidase respectively per ml of broth. A 200-ml portion of said culture broth was saturated to 75% with ammonium sulfate and the resultant precipitated fraction was collected by centrifugation and dissolved with a small amount of water and the resultant solution was tested for enzymatic activity. Consequently, there were recovered 83,000 units of β-amylase and 952 units of dextrin α-1,6-glucosidase.

EXAMPLE 5

Part of the enzyme solution obtained in Example 1 (having 10,000 units of β-amylase and 275 units of α-1,6-glucosidase) was allowed to react upon about 1 g of amylopectin at a concentration of 1% in the presence of $5 \times 10^{-3}$M of $CaCl_2$. The reaction was allowed to proceed at 40° C, with the pH value adjusted around 7. Reducing sugar in the reaction mixture was determined by the Somogyi & Nelson method. The test revealed that there was formed 972 mg of maltose. The amount of glucose formed was 3.7 mg. Paper chromatography conducted on the product showed a spot of maltose and a spot corresponding to a very small amount of maltotriose.

EXAMPLE 6

This example concerns a test which was performed on the production of maltose with a highly concentrated substrate, with a view of determining the optimal reaction temperature and the optimal reaction pH.

The reaction solution used in this case contained the components shown in Table 3 below at the indicated amounts.

Table 3

| | |
|---|---|
| Soluble starch (D.E. 1.5) | 1 g |
| Phosphate buffer (pH 6.5–7) or acetate buffer (pH 5–6) | 0.05 M |
| $CaCl_2$ | 0.01 M |
| β-amylase | 1,016 units |
| α-1,6-glucosidase | 13.1 units |
| Total volume | 10 ml |

To determine the effect of the pH value of the reaction solution, the reaction was performed at 50° C with the pH value varied to 5.0, 5.5, 6.0, 6.5 and 7.0. The results were as shown in Table 4.

Table 4

Maltose equivalent = ( $\frac{\text{Reducing sugar (as maltose)}}{\text{Dry substance}}$ ) × 100

| Reaction time (hours) | 2 | 8 | 24 | 36 | 48 | 72 |
|---|---|---|---|---|---|---|
| pH | | | | | | |
| 5.0 ± 0.1 | 49 | 70 | 73 | 74 | 77 | 76 |
| 5.5 ± 0.1 | 55 | 77 | 82 | 82 | 83 | 84 |
| 6.0 ± 0.1 | 63 | 83 | 92 | 94 | 97 | 100 |
| 6.5 ± 0.1 | 63 | 79 | 91 | 94 | 96 | 100 |
| 7.0 ± 0.1 | 59 | 78 | 89 | 91 | 92 | 96 |

To determine the effect of the temperature of reaction, the reaction was carried out of pH 6–6.5, with the reaction temperature varied to 40°, 50°, 55° and 60° C. The results were as shown in Table 5.

Table 5

| Reaction time (hours) | Maltose equivalent | | | | | |
|---|---|---|---|---|---|---|
| | 2 | 8 | 20 | 30 | 48 | 68 |
| Temp. (° C) | | | | | | |
| 40 | 64 | 79 | 82 | 87 | 94 | 100 |
| 50 | 66 | 78 | 85 | 92 | 97 | 100 |
| 55 | 70 | 78 | 82 | 83 | 87 | 89 |
| 60 | 68 | 70 | 71 | 72 | 73 | 74 |

EXAMPLE 7

A medium containing 1% of polypeptone, 1% of dextrin, 0.3% of $K_2HPO_4$ and 0.1% of $MgSO_4 \cdot 7H_2O$ and media obtained by adding to said medium varying amounts ($1 \times 10^{-7}$ to $1 \times 10^{-3}$ mole) of manganese sulfate as shown in Table 6 were prepared. These media were placed, each in the volume of 50 ml, in Erlenmeyer flasks having 200 ml capacity and sterilized by the ordinary method. Thereafter, Bacillus cereus var. mycoides was inoculated to the media and subjected to culture under aeration at 30° C for 42 hours.

After the culture, the culture broth was centrifuged and the resultant supernatant was assayed for produced β-amylase and dextrin α-1,6-glucosidase. The results thus obtained are shown in Table 6.

As is evident from this table, addition of manganese sulfate increased the amount of dextrin α-1,6-glucosidase produced up to about three times.

Table 6

| Amount of added manganese sulfate (mole) | Mycelia produced optical dencity (660 mμ) | Activity of dextrin α-1,6-glucosidase produced (units/ml broth) | Activity of β-amylase produced (units/ml broth) |
|---|---|---|---|
| 0 (not added) | 6.7 | 11.3 | 699 |
| $1 \times 10^{-7}$ | 6.5 | 14.2 | 678 |
| $1 \times 10^{-6}$ | 5.8 | 18.6 | 166 |
| $5 \times 10^{-6}$ | 5.6 | 23.4 | 155 |
| $1 \times 10^{-5}$ | 5.9 | 25.0 | 132 |
| $1 \times 10^{-4}$ | 5.9 | 28.3 | 152 |
| $1 \times 10^{-3}$ | 5.8 | 25.2 | 153 |

EXAMPLE 8

In Erlenmeyer flasks having 200 ml-capacity, 50 ml each of a medium containing 1% of polypeptone, 1% of dextrin, 0.3% of $K_2HPO_4$ and 0.1% of $MgSO_4 \cdot 7H_2O$ was placed and sterilized by the ordinary method. Thereafter, Bacillus cereus var. mycoides was inoculated to the medium and subjected to shaken culture at 30° C. At the 24th hour of culture at which the amount of β-amylase produced 237 units per ml of medium, manganese sulfate was sterilely added to the medium in an amount to give $1 \times 10^{-4}$ mole based on the medium, with the culture continued.

At the 42nd hour of culture, the culture was stopped. The culture broth was centrifuged to remove cells therefrom and the resultant supernatant was assayed for β-amylase activity and dextrin α-1,6-glucosidase activity. The results of the assay are shown in Table 7.

Table 7

| $MnSO_4$ | Culture time (hours) | Mycelia produced optical density (600 mμ) | Activity of β-amylase produced (unts/ml broth) | Activity of dextrin α-1,6-glucosidase produced(units/ml broth) |
|---|---|---|---|---|
| 0(None) | 42 | 6.7 | 377.6 | 13.0 |

Table 7-continued

| MnSO₄ | Culture time (hours) | Mycelia produced optical density (600 mμ) | Activity of β-amylase produced (unts/ml broth) | Activity of dextrin α-1,6-glucosidase produced(units/ml broth) |
|---|---|---|---|---|
| 1×10⁻⁴M MnSO₄ added at end of 24th hr. of culture | 24 | 6.5 | 236.8 | 12.5 |
|  | 42 | 6.6 | 244.5 | 22.2 |
| 1×10⁻⁴ ⁴M MnSO₄ added from beginning of culture | 42 | 5.9 | 28.8 | 25.0 |

As is evdent from this table, the manganese salt added to the medium halfway in the course of culture increased the amount of dextrin α-1,6-glucosidase produced to about 1.7 times and permitted simultaneous formation of β-amylase. When the culture was carried out in the medium which contained the manganese salt from the beginning, the amount of dextrin α-1,6-glucosidase produced was increased to about two times the amount obtainable in the absence of manganese salt and the amount of β-amylase produced was lowered to only 28.8 units/ml.

EXAMPLE 9

A medium containing 2% of polypeptone, 0.3% of $K_2HPO_4$, 0.1% of $MgSO_4 \cdot 7H_2O$ and $5 \times 10^{-4}M$ of $CaCl_2$ and media having sodium citrate added to said medium in amounts corresponding to concentrations of 0.5 and 1% and media having sodium tartrate added to said medium in amounts corresponding to concentrations of 0.25 and 0.5% were prepared. In Erlenmeyer flasks having 200 ml-capacity, portions of the media, each in the amount of 50 ml, were placed and sterilized by the ordinary method. Subsequently, *Bacillus cereus* var. *mycoides* was inoculated to the media and subjected to shaken culture at 30° C for 42 hours.

After the culture, the culture broth was centrifuged and the resultant supernatant was assayed for β-amylase activity and dextrin α-1,6-glucosidase activity. The results thus obtained are shown in Table 8.

TABLE 8

| Organic acid added | Amount added (% of medium) | Mycelia produced optical density (660 mμ) | Activity of β-amylase produced (units/ml broth) | Activity of dextrin α-1,6-glycosidase produced (units/ml broth) |
|---|---|---|---|---|
| Sodium citrate | 0.5 | 4.9 | 1,035.0 | 20.7 |
| Sodium citrate | 1.0 | 4.8 | 1,080.0 | 17.1 |
| Sodium tartarate | 0.25 | 4.7 | 1,119.0 | 18.4 |
| Sodium tartarate | 0.5 | 4.9 | 1,063.0 | 16.2 |
| Control (not added) |  | 4.9 | 588.0 | 13.0 |

It is clear from the table that the addition of organic acid notably increased the amounts of β-amylase and dextrin α-1,6-glucosidase produced.

EXAMPLE 10

In two jar fermentors having 10 liter-capacity, a medium containing 4% of Milk-casein, 0.3% of $K_2HPO_4$, 0.1% of $MgSO_4 \cdot 7H_2O$, $5 \times 10^{-4}M$ of $CaCl_3$ and 0.5% of soluble starch was placed, each in the volume of 5 liters. Rape-seed cake was added to one of the two jar fermentors in an amount corresponding to 4% based on the medium. Then, the media in the two fermentors were sterilized for 30 minutes at 121° C. Thereafter, *Bacillus cereus* var. *mycoides* (100 ml) was inoculated and subjected to aerated culture at 30° C, with the air supplied at a flow rate of 5 liters/min. and the agitation given at a rate of 250 rpm. After 24 hours of the culture, the culture broth was centrifuged and the resultant supernatant was assayed for enzymatic activity. The results thus obtained are shown in Table 9.

TABLE 9

| Rape-seed cake (% of medium) | Activity of β-amylase produced (units/ml broth) | Activity of dextrin α-1,6-glucosidase produced (units/ml broth) |
|---|---|---|
| 4.0 | 2,470.0 | 106.0 |
| Control (not added) | 2,600.0 | 44.4 |

As is clear from the table, in the culture carried out in the medium containing the rape-seed cake, the amount of dextrin α-1,6-glucosidase produced was about 2.4 times as large as the amount produced in the medium not containing the rape-seed cake.

The culture broth resulting from the medium containing the rape-seed cake was centrifuged to remove the cells. Two liters of the resultant supernatant was combined with 4 liters of cold ethanol to cause precipitation of enzymes. The precipitate thus formed was recovered by filtration and then dried. Consequently, there was obtained a powdery composite enzyme consisting of 115,800 units of β-amylase and 4,640 units of dextrin α-1,6-glucosidase respectively per g, indicating that the recovery ratio of β-amylase was 75% and that of dextrin α-1,6-glucosidase was 70% respectively.

EXAMPLE 11

With caustic soda, 8% corn steep liquor (having about 4% solids content) was adjusted to pH 7.5. The resultant mixture was centrifuged to remove precipitation (including a substance inhibiting the growth of β-amylase) occurring in consequence of the pH adjustment. In Erlenmeyer flasks having 200 ml-capacity, 50 ml each of the supernatant was placed and, after having 0.5% of starch added thereto, sterilized by the conventional method. Thereafter, Bacillus cereus var. mycoides was inoculated and subjected to culture aerobically at 30° C for 42 hours. At the end of the culture, the culture broth was centrifuged to remove cells and the supernatant was assayed for produced β-amylase and dextrin α-1,6-glucosidase. The results are shown in Table 10.

TABLE 10

|  | Activity of β-amylase produced (units/ml broth) | Activity of dextrin α-1,6-glucosidase produced (units/ml broth) |
|---|---|---|
| Control | 52.1 | 35.3 |
| Removal of substance inhibiting growth of β-amylase | 592.7 | 41.1 |

As is evident from the table, when the culture was carried out in the corn steep liquor which had been stripped of the precipitate caused by pH adjustment, the amount of β-amylase produced in the culture was notably increased.

EXAMPLE 12

A mixture of 10 g of soluble starch with one liter of an enzyme solution obtained by cultivating Bacillus cereus var. mycoides and containing 572 units of β-amylase and 43.5 units of dextrin α-1,6-glucosidase was mixed with 40 g of an activated carbon (Norit marketed by Wako Pure Chemicals) and agitated to have the enzymes adsorbed on the activated carbon. The enzymes were recovered by filtration.

The enzyme activities of the filtrate and the activated carbon having the enzymes adsorbed thereon were assayed. The results are shown in Table 11.

Table 11

|  | β-amylase | dextrin α-1,6-glucosidase |
|---|---|---|
| (A) Amount added | 572,000(units) | 43,500(units) |
| (B) Amount unadsorbed | 197,000(units) | 9,700(units) |
| (C) Immobilized enzyme activity | 338,000(units) | 33,800(units) |
| Yield of immobilized enzyme (C/A−B × 100) | 90.1% | 100% |

It is seen from the table that, as enzymes, β-amylase was recovered in a yield of 90.1% and dextrin α-1,6-glucosidase in a yield of almost 100% respectively, both in the form of immobilized enzyme. When no starch was added, however, the yield of β-amylase as immobilized enzyme was about 12.4%.

Part of the immobilized enzyme (3,000 units of β-amylase and 310 units of dextrin α-1,6-glucosidase) was added to 10 g of soluble starch and the resulting mixture was made up to a total volume of 100 ml with water. The solution was then brought to and kept at 50° C, with the pH value in the range of 6–6.5, to carry out reaction. After the completion of this reaction, the solution was assayed for sugar composition, which was found to be 90.5% of maltose, 7.5% of maltotriose and 2.0% of oligosaccharide.

EXAMPLE 13

In 100 ml of water, 50 g of corn starch and 10 g of Celite were added and agitated and, then, subjected to heat treatment at 60° C for 30 minutes. To the resultant solution, 300 ml of a culture filtrate of Bacillus cereus var. mycoides (pH 7.1, 403 units of β-amylase/ml and 28.0 units of dextrin α-1,6-glucosidase/ml) was added and agitated to have the two enzymes adsorbed.

Then the mixture was filtered to recover the enzymes, which were tested for activity. The results obtained are shown in Table 12.

Table 12

|  | β-amylase | dextrin α-1,6-glucosidase |
|---|---|---|
| (A) Original activity | 121,000(units) | 8,400(units) |
| (B) Remaining activity | 111,000(units) | 1,860(units) |
| (C) Fixed enzyme activity | 95,300(units) | 6,220(units) |
| Yield of fixed enzyme (C/A−B × 100) | 86.7% | 95.1% |

The mixture of starch and Celite having both enzymes adsorbed thereon was subsequently added to a 10% aqueous solution of dextrin containing 10% of sodium chloride to effect elution of the enzymes from the adsorbents. Consequently, β-amylase and dextrin α-1,6-glucosidase were recovered at yields of 100 and 85% respectively.

EXAMPLE 14

Filtrate, each 100 ml in volume, of culture of Bacillus cereus var. mycoides containing 758 units of β-amylase and 37.1 units of dextrin α-1,6-glucosidase per ml were mixed with 5 g each of acid clay, bentonite, talcum, Celite and Perlite to cause adsorption of dextrin α-1,6-glucosidase.

The adsorbed enzyme was recovered by filtration or by centrifugation, washed thoroughly with water and then tested for activity. The results obtained are shown in Table 13.

Table 13

|  | Adsorbed dextrin α-1,6-glucosidase (u/g) | Adsorbed β-amylase(u/g) |
|---|---|---|
| Acid Clay | 612 | 790 |
| Bentonite | 648 | 694 |
| Talcum | 416 | 200 |
| Celite | 492 | 0 |
| Perlite | 532 | 0 |

It is seen from the table that dextrin α-1,6-glucosidase was satisfactorily adsorbed by all the adsorbents tested and the amount adsorbed was in the range of from 400 to 700 units per gram.

EXAMPLE 15

To 100 g (dry weight) of liquefied starch of DE 1.5%, 30,000 units of β-amylase, 3,000 units of dextrin α-1,6-glucosidase and 0.73% of $CaCl_2·2H_2O$ were added. The mixture was diluted to a total volume of 500 ml and brought to and kept at 50° C, with the pH value in the range of 6–6.5, to effect reaction. After 100 hour reaction, the sugar composition of the reaction mixture was assayed by paper chromatography. The sugar composition was determined to be 90.6% of maltose, 7.1% of maltotriose, 0.0% of glucose and 2.3% of other saccharides.

What is claimed is:

1. A method for the simultaneous manufacture of β-amylase and α-1,6-glucosidase from a microorganism, which comprises:
   culturing a microorganism selected from the group consisting of *Bacillus cereus* var. *mycoides* (ATCC No. 31102), *Bacillus* sp. YT 1002 (ATCC No. 31101) and *Bacillus* sp. YT 1003 (ATCC No. 31103) which belong to the genus Bacillus having the ability to produce β-amylase and α-1,6-glucosidase simultaneously in a culture medium; and
   recovering the -amylase and α-1,6-glucosidase from the culture broth.

2. The method according to claim 1, wherein manganese ions are introduced into the culture medium to promote the production of dextrin α-1,6-glucosidase.

3. The method according to claim 1, wherein the culture of the microorganism is conducted in a culture medium which contains rape seed, rape-seed cake or extract thereof to promote the 4. The method according to claim 1, wherein an organic acid is introduced into the culture medium to promote the production of dextrin α-1,6-glucosidase and β-amylase.

5. The method according to claim 4, wherein the organic acid is citrate.

6. The method according to claim 4, wherein the organic acid is tartarate.

7. The method according to claim 1, wherein the culture of the microorganism is carried out in a medium prepared by adjusting corn steep liquor to pH 6 to 9 and subsequently removing the resultant precipitate therefrom.

8. A method for the manufacture of maltose from starch or its derivatives with enzymes by a microoganism, which comprises:
   culturing a microorganism selected from the group consisting of *Bacillus cereus* var. *mycoides* (ATCC No. 31102), *Bacillus* sp YT 1002 (ATCC No. 31101) and *Bacillus* sp. YT 1003 (ATCC No. 31103) which belong to genus Bacillus having the ability to produce β-amylase and α-1,6-glucosidase simultaneously in a culture medium; recovering said enzymes thus produced from the culture broth;
   adding said enzymes to said starch or its derivatives; and
   reating the resultant mixture under conditions such that said enzymes promote the hydrolysis of starch to maltose.

9. The method according to claim 8, wherein said resultant mixture is reacted at 40° to 60° C at a pH of 5 to 8.

* * * * *